| United States Patent [19] | [11] | 4,346,242 |
|---|---|---|
| Spatz | [45] | Aug. 24, 1982 |

[54] METHOD FOR PREPARING SUBSTITUTED META-PHENYLALKOXYNITROBENZENES

[75] Inventor: David M. Spatz, San Francisco, Calif.

[73] Assignee: American Cyanamid Company, Stamford, Conn.

[21] Appl. No.: 156,881

[22] Filed: Jun. 5, 1980

[51] Int. Cl.$^3$ .............................................. C07L 41/01
[52] U.S. Cl. .................................. 568/586; 568/585; 568/44; 260/465 F; 564/441; 564/26; 564/52; 71/99; 71/120
[58] Field of Search ........................ 568/585, 586, 44; 260/465 F; 564/441

[56] References Cited

U.S. PATENT DOCUMENTS

| 2,159,025 | 5/1939 | Hester | 568/585 |
|---|---|---|---|
| 2,213,215 | 9/1940 | Hester | 568/585 X |
| 2,243,479 | 5/1941 | Hester | 568/585 X |
| 3,207,786 | 9/1965 | Yale et al. | 568/585 X |
| 3,387,041 | 6/1968 | Oscar | 568/585 |
| 4,168,388 | 9/1979 | Lavagnino et al. | 568/585 X |

FOREIGN PATENT DOCUMENTS 40-9136  5/1965  Japan .................... 568/585

*Primary Examiner*—Bernard Helfin
*Attorney, Agent, or Firm*—Thomas J. Monahan; H. G. Jackson

[57] ABSTRACT

Methods for the preparation of substituted meta-phenylalkoxynitrobenzenes and their use as starting materials for the synthesis of herbicidal meta-phenylalkoxyphenylurea.

9 Claims, No Drawings

METHOD FOR PREPARING SUBSTITUTED META-PHENYLALKOXYNITROBENZENES

The invention relates to methods for the preparation of compounds of formula (I):

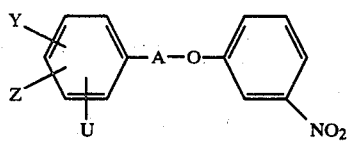

wherein Y is hydrogen, halogen, $C_1$-$C_4$ alkyl, $C_3$-$C_5$ alkenyl, $C_3$-$C_5$ alkynyl, $C_1$-$C_4$ alkoxy, $CH_3S$, $CF_3$, $CN$, $NH_2$, $OCF_2H$, $OCF_3$, or $OCF_2Cl$; Z is hydrogen, $C_1$-$C_4$ alkyl, $C_1$-$C_4$ alkoxy, halogen, or $CF_3$; U is hydrogen, $C_1$-$C_4$ alkyl, $C_1$-$C_4$ alkoxy or halogen; A is $C_2$-$C_4$ alkylene, straight chain or branched.

A preferred group of compounds of formula (I) are those wherein Y is hydrogen, halogen, $CH_3$ or $CH_3O$; Z and U are each hydrogen, and A is as hereinabove defined.

The most preferred compounds are:

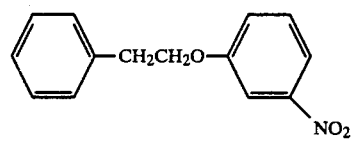

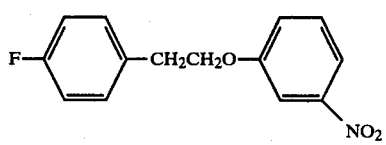

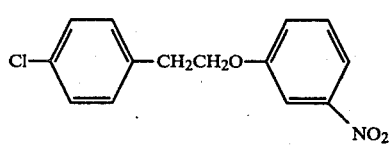

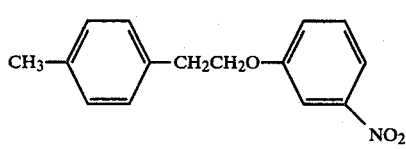

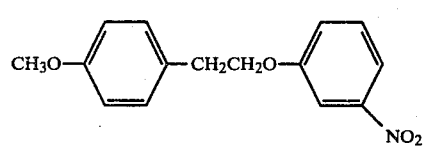

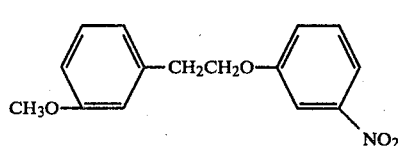

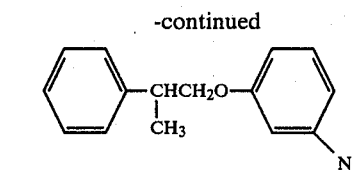

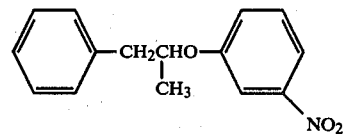

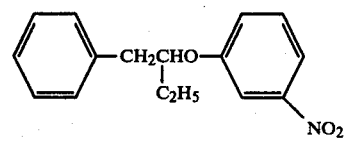

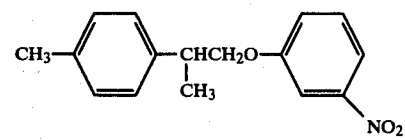

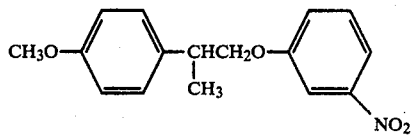

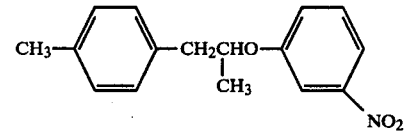

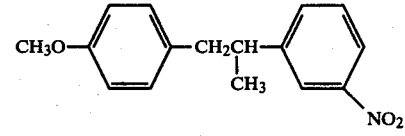

or

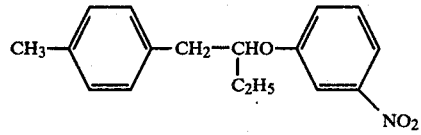

This invention also relates to novel compounds of the following formula:

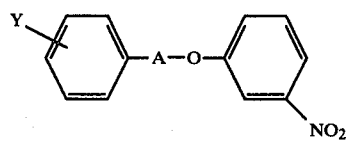

wherein Y is halogen, $C_1$-$C_4$ alkyl, $C_3$-$C_5$ alkenyl, $C_3$-$C_5$ alkynyl, $C_1$-$C_4$ alkoxy, $CH_3S$, $CF_3$, $CN$, $NH_2$, $OCF_2H$, $OCF_3$ or $OCF_2Cl$; A is $C_2$-$C_4$ alkylene, straight chain or branched.

The compounds of formula (I) as defined and described above are useful and valuable intermediates for the preparation of herbicidal meta-(phenylalkoxy)phenylurea compounds of formula (II):

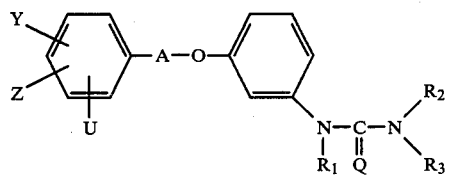

which are disclosed and claimed in co-pending U.S. applications Ser. Nos. 30,675 and 30,676 filed Apr. 11, 1979 and Apr. 16, 1979 and both now abandoned, respectively, wherein Q is O or S; Y is hydrogen, halogen, $C_1$–$C_4$ alkyl $C_2$–$C_5$ alkenyl, $C_2$–$C_5$ alkynyl, $C_1$–$C_4$ alkoxy, $CH_3S$, $CF_3$, CN, $NH_2$, $OCF_2H$, $OCF_3$, or $OCF_2Cl$; Z is hydrogen, $C_1$–$C_4$ alkyl, $C_1$–$C_4$ alkoxy, halogen or $CF_3$; U is hydrogen, $C_1$–$C_4$ alkyl, $C_1$–$C_4$ alkoxy or halogen; A represents a $C_2$–$C_4$ carbon chain which may be straight or branched; $R_1$ is hydrogen, $CH_3$ or CHO; $R_2$ is $C_1$–$C_2$ alkyl optionally substituted with halogen, $C_3$–$C_4$ alkenyl or $C_3$–$C_4$ alkynyl; $R_3$ is hydrogen, $C_1$–$C_2$ alkyl or CHO, and when $R_2$ and $R_3$ are taken together with the nitrogen they are attached to, they represent a moiety

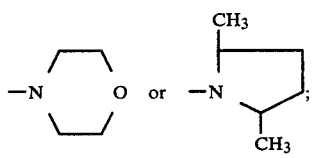

with the proviso, that at least one of $R_1$, $R_2$ and $R_3$ must be hydrogen or CHO.

Hitherto, phenylurea compounds of formula (II) were customarily prepared by a synthetic route shown and discussed below in broad outline:

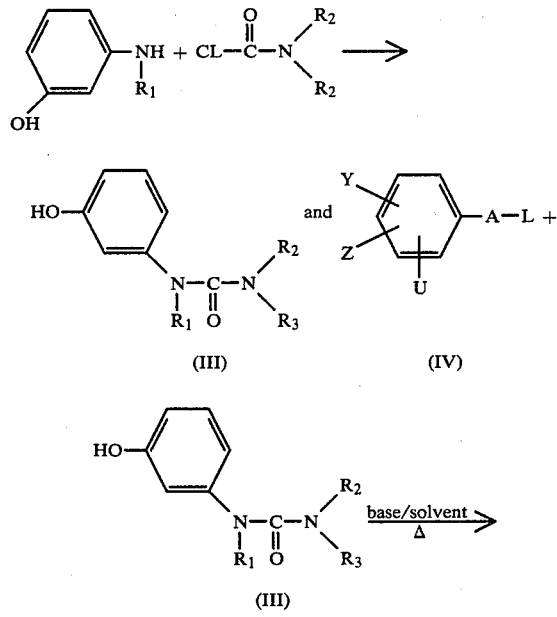

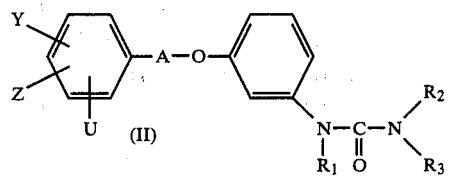

wherein Y, Z, U, $R_1$, A, $R_2$ and $R_3$ are as hereinabove defined, and L is $-OSO_2CH_3$ or halide. Thus, the appropriately substituted methanesulfonate ester of a phenylalkanol or the corresponding phenylalkyl halide of formula (IV) is reacted with an ureidophenol of formula (III) in the presence of an organic or inorganic base, preferably potassium t-butoxide, and a solvent such as dimethylformamide (DMF) in the temperature range of 20° C. to 90° C., and preferably 60° C. to 80° C., for a period of time sufficient to essentially complete the reaction.

It has now been found that the desirable intermediates of formula (I) may be conveniently prepared by a synthetic route illustrated and discussed in the following:

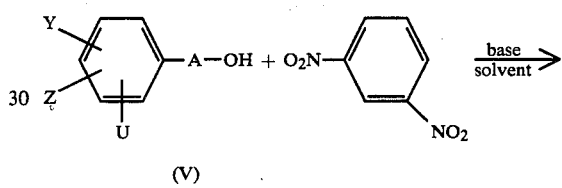

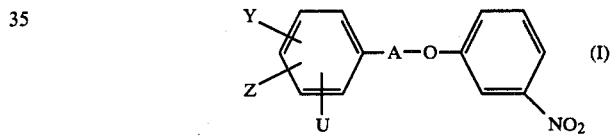

wherein A, Y, Z and U are as hereinabove defined.

Thus, a phenylalkanol of formula (V) is reacted with an equimolar or excess amount of m-dinitrobenzene in the presence of an equimolar amount of a base such as sodium-, potassium-, or lithium hydroxide or t-butoxide in an anhydrous polar solvent such as hexamethylphosphoramide (HMPA), dimethylformamide (DMF), dimethyl sulfoxide (DMSO), acetonitrile or mixtures thereof in a temperature range of from about 20° C. to about 80° C., (preferably 20°–30° C.) for a period of time sufficient to essentially complete the reaction. Preferably, the above reaction is carried out under a blanket of inert gas, such as nitrogen. On completion of the reaction the product is isolated and purified by standard laboratory procedures such as recrystallization, vacuum distillation, column chromatography and the like. The thus obtained product is next reduced to the corresponding amino compound (VI), for instance, with hydrogen gas using a palladium on carbon catalyst and an inert solvent.

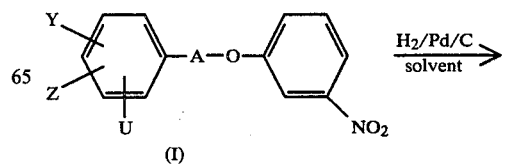

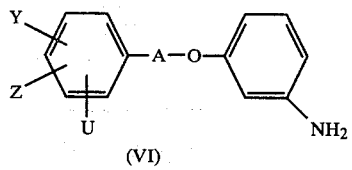

(VI)

Treating the above aniline (VI) with concentrated formic acid yields the formanilide (VII):

VI + HCOOH 

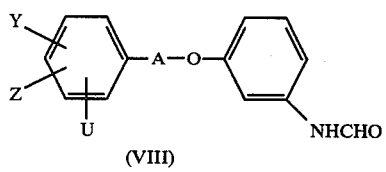

(VIII)

The formanilide (VII) may be reduced, for instance, with lithium aluminum hydride to the corresponding N-methylaniline of formula (VIII):

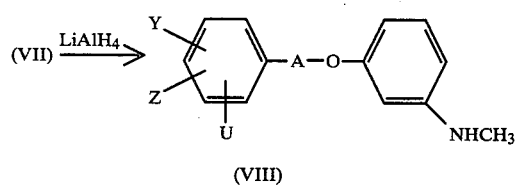

(VIII)

Compounds VII and VIII, when reacted with isocyanates yield formula II ureas, wherein $R_1$ is formyl or methyl, respectively.

Reacting the aniline VI with phosgene or thiophosgene, yields the corresponding isocyanate or isothiocyanate IX which reacts with N-alkylformamides to afford formula (II) compounds, wherein $R_3$ is CHO, as shown below: or with Q=S with amines of formula

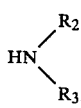

to give thioureas:

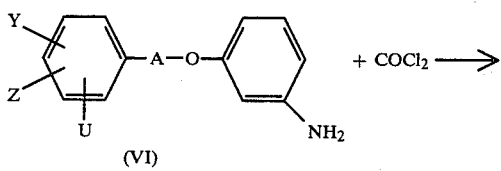

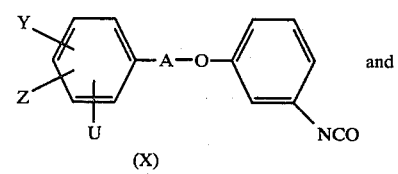

(X) + OHC—NH—$R_2$ 

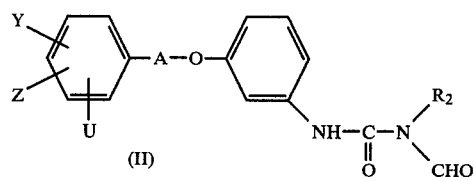

(II)

Reacting a compound of formula VI, VII or VIII with a carbamyl chloride of formula

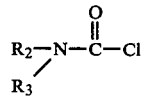

yields a herbicidal urea of formula (II)

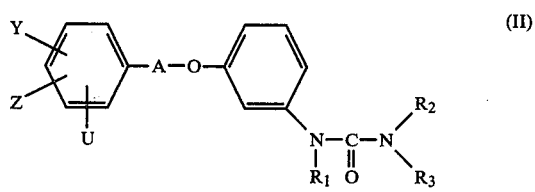

wherein $R_1$ is hydrogen, formyl or methyl, respectively.

The meta-phenylalkoxyphenylurea compounds of formula (II) show not only excellent broadleaf weed control when applied postemergence, but also show an unexpected and useful degree of crop tolerance to wheat, barley, rice, corn, soybeans, and especially sorghum. Crop selectivity may be further modified by applying these compounds to said crops at different growth stages. The above compounds also show preemergence herbicidal activity coupled with selectivity, albeit at somewhat higher rates than needed for postemergence control. Additionally, some of the above compounds are also found to control grasses when applied pre- or postemergence at rates higher than those used for pre- or postemergence control of broadleaf weeds.

In practice, the active compounds of formula (II) are generally formulated as dusts, dust concentrates, wettable powders, emulsion concentrates, and the like.

In using wettable powders, emulsion concentrates, and the like, the formulated material is generally dispersed in water and applied at the rate of from 0.03 kg per hectare to about 2 kg per hectare to the plants or to soil containing the seeds of the plants.

The invention is further illustrated by the the following examples which are not to be taken as being limitative thereof.

EXAMPLE 1

Preparation of 3-phenylethyloxynitrobenzene

Potassium t-butoxide (11.2 g; 0.1 mol) is added under a nitrogen atmosphere to a stirred mixture of m-dinitrobenzene (16.8 g; 0.1 mol), phenethyl alcohol (12.2 g; 0.1 mol) and hexamethylphosphoramide (HMPA; 200 ml). Almost instantly a dark red color develops and then slowly fades in the course of the reaction and turns black. The reaction mixture is stirred for 7 days at room temperature. It is then drowned in water, and extracted twice with methylene chloride (500 ml). The methylene chloride solution is washed with water (3X), saturated brine (1X), dried over magnesium sulfate and evaporated to yield 53.5 g of a dark oil. Additional solvent (HMPA) and some m-dinitrobenzene is removed from the oil by heating same at about 90° C. under 0.5 mm vacuum. The residual oil (~25 g) is chromatographed on 1 kg silica gel with 3:1 hexane:methylene chloride. Collected fractions, containing the same material by thin layer chromatography, are combined and evaporated to afford 7.4 g (30%) of product, a light yellow oil. On standing, the oil crystallizes, mp. 46.5°–49° C.

By the above procedure, but substituting 4-methylphenylethyl alcohol, 4-methoxyphenylethyl alcohol, 4-chlorophenylethyl alcohol, 3-methoxyphenylethyl alcohol, 4-fluorophenylethyl alcohol, 3-phenylpropoxy alcohol, 4,α-dimethylphenylethyl alcohol, 4,β-dimethylphenylethyl alcohol or 4-methyl-α-ethylphenylethyl alcohol for phenylethyl alcohol, the corresponding substituted phenylethyloxynitrobenzenes and 3-(3-phenylpropoxy)nitrobenzene can be obtained, respectively.

EXAMPLE 2

Postemergence Herbicidal Activity

The postemergence herbicidal activity of the m-phenylalkoxyphenylureas prepared from the compounds of the present invention is demonstrated by the following tests, wherein a variety of monocotyledonous and dicotyledonous plants are treated with test compounds dispersed in aqueous acetone mixtures. In the tests, seedling plants are grown in separate cups for about 2 weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.032 kg to 2.0 kg per hectare of active compound when applied to the plants through a spray nozzle operating at 2.81 kg/cm² pressure for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in Table I below, wherein it can be seen that these compounds effectively control broadleaf weeds in general, and selected compounds also control grasses at higher rates of application.

| RATING SYSTEM | |
|---|---|
| Rating: | % Control (Compared to Check) |
| 9 - Complete kill | 100 |
| 8 - Approaching complete kill | 91–99 |
| 7 - Good herbicidal effect | 80–90 |
| 6 - Herbicidal effect | 65–79 |
| 5 - Definite injury | 45–64 |
| 4 - Injury | 30–44 |
| 3 - Moderate effect | 10–29 |
| 2 - Slight effect | 6–15 |
| 1 - Trace effect | 1–5 |
| 0 - No effect | 0 |
| X - Missing data | — |

The above rating scale is based upon a visual observation of plant stand, vigor, malformation, size, chlorosis, and overall plant appearance as compared with a control.

A rating of "X" is given if effects on plant growth caused by chemical treatment cannot be clearly determined as a result of disease, failure to germinate or grow, or where the plants were not present in a particular test at a particular rate because of shortage of plant material.

| PLANT ABBREVIATIONS | | |
|---|---|---|
| Code | Common Name | Scientific Name |
| BA | Barnyardgrass | (*Echinochloa crusgalli*) |
| CR | Crabgrass | (*Digitaria sanguinalis*) |
| FO | Green Foxtail | (*Setaria viridis*) |
| NS | Nutsedge | (*Cyperus rotundus*) |
| WO | Wild Oat | (*Avena fatua*) |
| CB | Cocklebur | (*Xanthium pensylvanicum*) |
| JW | Jimsonweed | (*Datura stramonium*) |
| LA | Lambsquarters | (*Chenopodium album*) |
| MG | Morningglory | (*Ipomoea spp.*) |
| MU | Mustard, Wild | (*Brassica kaber*) |
| PI | Pigweed | (*Amaranthus retroflexus*) |
| RW | Ragweed | (*Ambrosia artemisiifolia*) |
| VL | Veletleaf | (*Abutilon theophrasti*) |
| BY | Barley | (*Hordeum vulgare*) |
| CN | Corn | (*Zea mays*) |
| RI | Rice | (*Oryza sativa*) |
| SO | Sorghum, Grain | (*Sorghum bicolor*) |
| SY | Soybean | (*Glycine max*) |
| WH | Wheat | (*Triticum aestivum*) |

TABLE I

Evaluation of the Postemergence Herbicidal Activity of the Compounds of the Invention

| Compound | Rate kg/ha | BA | CR | FO | NS | WO | CB | JW | LA | MG | MU |
|---|---|---|---|---|---|---|---|---|---|---|---|
| 1,1-Dimethyl-3-[3-(phenylethyloxy)-phenyl]urea | 2.0 | 2 | | 9 | 0.5 | 5.5 | 9 | 9 | 9 | 9 | 9 |
| | 1.0 | 1.0 | 1 | 5.0 | 0 | 5.7 | 9.0 | 8.0 | 9.0 | 9.0 | 9.0 |
| | 0.5 | 0.0 | 0 | 2.5 | 0 | 4.0 | 9.0 | 7.0 | 9.0 | 9 | 9.0 |
| | 0.25 | 0.0 | 0 | 1.0 | 0 | 4.0 | 9.0 | 6.0 | 9.0 | 9.0 | 8.5 |
| | 0.125 | 0.0 | 0 | 0.5 | 0 | 1.5 | 9.0 | 5.0 | 7.5 | 6.0 | 8.0 |
| | 0.063 | 0.0 | 0 | 0.0 | 0 | 0.5 | 5.5 | 3.5 | 6.0 | 2.5 | 6.0 |
| | 0.032 | 0 | 0 | 0 | | 0 | 3 | 0 | 2 | 0 | 9 |
| 1,1-Dimethyl-3-[3-(3-phenylpropoxy)phenyl]-urea | 2.0 | 0.5 | | 2.5 | 0 | 1 | 9 | 8.0 | 9 | 9 | 9 |
| | 1.0 | 0.3 | 0 | 1.3 | 0 | 2.8 | 9.0 | 7.8 | 9.0 | 9.0 | 9.0 |
| | 0.5 | 0.0 | 0 | 1.0 | 0 | 1.8 | 9.0 | 7.5 | 8.7 | 8.3 | 9.0 |
| | 0.25 | 0.0 | 0 | 1.0 | 0 | 0.7 | 9.0 | 5.7 | 8.7 | 8.3 | 8.7 |
| | 0.125 | 0.0 | 0 | 0.7 | 0 | 0.3 | 7.0 | 5.0 | 6.0 | 4.3 | 8.0 |
| | 0.063 | 0.0 | 0 | 0.3 | 0 | 0.0 | 5.0 | 2.0 | 4.0 | 2.7 | 6.3 |
| | 0.032 | 0.0 | 0 | 0 | | 0 | 5 | 0 | 3 | 0 | 9.0 |
| 3-[3-(4-Fluorophenylethyloxy)-phenyl]-1,1-dimethylurea | 2.0 | 0 | 9 | 9 | | 3 | 9 | 9 | 9 | 9 | 9 |
| | 1.0 | 0 | 6 | 9 | | 1 | 9 | 9 | 9 | 9 | 9 |
| | 0.5 | 0 | 3 | 9 | | 0 | 9 | 9 | 9 | 3 | 9 |
| | 0.25 | 0 | 2 | 7 | | 0 | 9 | 9 | 9 | 2 | 9 |
| | 0.125 | 0 | 0 | 3 | | 0 | 9 | 9 | 9 | 0 | 9 |

TABLE I-continued
Evaluation of the Postemergence Herbicidal Activity of the Compounds of the Invention

| Compound | Rate kg/ha | PI | RW | VL | BY | CN | CO | RI | SO | SY | WH |
|---|---|---|---|---|---|---|---|---|---|---|---|
| 1,1-Dimethyl- | 2.0 | 9 | 9 | 8 | 7 | 8.5 |  | 4 | 2 | 7.0 | 4 |
| 3-[3-(phenyl- | 1.0 | 9.0 | 9.0 | 7.5 | 5.5 | 5.7 | 9 | 3.5 | 2 | 6.3 | 4.5 |
| ethyloxy)- | 0.5 | 9.0 | 9.0 | 4.5 | 3.0 | 5.0 | 3 | 3.0 | 1 | 4.0 | 2.5 |
| phenyl]urea | 0.25 | 6.0 | 7.0 | 3.0 | 2.0 | 3.0 | 6 | 2.0 | 1 | 2.0 | 1.0 |
|  | 0.125 | 3.5 | 3.5 | 1.0 | 0.5 | 1.0 |  | 0.5 | 1 | 1.5 | 0.0 |
|  | 0.063 | 1.5 | 3.0 | 0.5 | 0.0 | 0.0 | 0 | 0.0 | 0 | 1.0 | 0.0 |
|  | 0.032 | 0 | 0 | 0 | 0 | 0 | 0 | 0 |  | 0 | 0 |
| 1,1-Dimethyl- | 2.0 | 9 | 9 | 4.0 | 6 | 4.5 |  | 2.0 | 1.5 | 6.3 | 1.5 |
| 3-[3-(3-phenyl- | 1.0 | 9.0 | 9.0 | 4.3 | 4.5 | 3.5 | 9.0 | 3.3 | 1.0 | 4.0 | 2.0 |
| propoxy)phenyl]- | 0.5 | 9.0 |  | 0.0 | 2.5 | 3.5 | 9.0 | 3.3 | 0.5 | 3.0 | 1.7 |
| urea | 0.25 | 9.0 |  | 0.0 | 2.5 | 2.0 | 6.0 | 1.0 | 0.5 | 2.7 | 1.3 |
|  | 0.125 | 8.0 |  | 0.0 | 1.5 | 0.3 | 6.0 | 0.7 | 0 | 1.3 | 0.0 |
|  | 0.063 | 2.7 |  | 0.0 | 0.5 | 0.3 |  | 0.3 | 0 | 0.7 | 0.0 |
|  | 0.032 | 1.0 |  | 0 | 0 | 0.0 |  | 1.0 |  | 0.0 | 0.0 |
| 3-[3-(4-Fluoro- | 2.0 | 9 | 9 | 9 |  | 3 | 9 | 6 | 2 | 9 | 5 |
| phenylethyloxy)- | 1.0 | 9 | 9 | 6 |  | 3 | 9 | 4 | 1 | 9 | 5 |
| phenyl]-1,1- | 0.5 | 9 | 9 | 2 |  | 3 | 9 | 3 | 0 | 6 | 4 |
| dimethylurea | 0.25 | 9 | 9 | 0 |  | 6 | 9 | 2 | 0 | 2 | 3 |
|  | 0.125 | 9 | 9 | 0 |  | 3 | 3 | 1 | 0 | 2 | 1 |
|  | 0.063 | 2 | 7 | 0 |  | 1 | 3 | 0 | 0 | 0 | 1 |
|  | 0.032 |  |  |  |  |  |  |  |  |  |  |

In the above Table, numbers without decimals represent the result of a single test, while numbers with decimals represent the averages of two or more replicates.

EXAMPLE 3
Preemergence Herbicidal Activity

The preemergence herbicidal activity of the m-phenylalkoxyphenylureas prepared from the compunds of the present invention is exemplified by the following tests in which the seeds or propagating organs of a variety of monocotyledonous and dicotyledonous plants are separately mixed with potting soil and planted on top of approximately 2.5 cm of soil in separate cups or planted on soil surface and covered with approximately 1.25 cm of soil. After planting, the cups are sprayed with the selected aqueous acetone solution containing test compound in sufficient quantity to provide the equivalent of about 0.07 to 2.0 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system set forth in Example 2. The data obtained are reported in Table II below, wherein it can be seen that these compounds control broadleaf weeds, and selected compounds also control grasses when applied preemergence at higher rates.

TABLE II
Evaluation of the Preemergence Herbicidal Activity of the Compounds of the Invention

| Compound | Rate kg/ha | BA | CR | FO | WO | CB | JW | LA | MG | MU | PI | RW | VL | BY | CN | CO | RI | SO | SY | WH |
|---|---|---|---|---|---|---|---|---|---|---|---|---|---|---|---|---|---|---|---|---|
| 1-1-Di- | 2.0 |  |  |  | 0 | 6 | 0 |  |  |  |  |  |  |  |  |  |  |  |  |  |
| methyl- | 1.0 | 0 | 0 | 5 | 0 | 0 | 4.5 | 9 | 0 | 9 | 9 | 9 | 0 | 0 | 0 | 0 | 0 |  | 0 | 0 |
| 3-[3- | 0.5 | 0 | 0 | 2 | 0 | 0 | 3.0 | 9 | 0 | 9 | 9 | 9 | 0 | 0 | 0 | 0 | 0 |  | 0 | 0 |
| (phenyl- | 0.25 | 0 | 0 | 0 | 0 | 0 | 1.0 | 7 | 0 | 3 | 2 | 1 | 0 | 0 | 0 | 0 | 0 |  | 0 | 0 |
| ethyloxy)- |  |  |  |  |  |  |  |  |  |  |  |  |  |  |  |  |  |  |  |  |
| phenyl] |  |  |  |  |  |  |  |  |  |  |  |  |  |  |  |  |  |  |  |  |
| urea |  |  |  |  |  |  |  |  |  |  |  |  |  |  |  |  |  |  |  |  |
| 1,1-Di- | 2.0 |  |  | 0 | 0.0 | 0.5 | 4.5 | 9.0 | 0 | 9.0 | 9.0 | 3.0 | 0.0 |  |  | 0.0 | 0.0 | 0 | 0.0 | 0 |
| methyl- | 1.0 | 0 | 0 | 0.0 | 0.0 | 0.0 | 5.0 | 8.5 | 0.0 | 8.5 | 9.0 | 3.0 | 0.0 | 0.0 | 0 | 0.0 | 0.0 | 0 | 0.0 | 0.0 |
| 3-[3-(3- | 0.5 | 0 | 0 | 0.0 | 0.0 | 0.0 | 3.7 | 9.0 | 0.0 | 7.5 | 9.0 | 1.5 | 0.0 | 0.0 | 0 | 0.0 | 0.0 | 0 | 0.0 | 0.0 |
| phenyl- | 0.25 | 0 | 0 | 0.0 | 0.0 | 0.0 | 4.5 | 8.0 | 0.0 | 6.0 | 3.0 | 0.5 | 0.0 | 0.0 | 0 | 0.0 | 0.0 | 0 | 0.0 | 0.0 |
| propoxy)- | 0.0125 | 0 | 0 | 0.0 | 0.0 | 0.0 | 4.5 | 7.0 | 0.0 | 5.5 | 1.0 | 0.0 | 0.0 | 0.0 | 0 | 0.0 | 0.0 | 0 | 0.0 | 0.0 |
| phenyl]- | 0.063 | 0 | 0 | 0.0 | 0.0 | 0.0 | 0.0 | 6.0 | 0.0 | 4.5 | 0.0 | 0.0 | 0.0 | 0.0 | 0 | 0.0 | 0.0 | 0 | 0.0 | 0.0 |
| urea |  |  |  |  |  |  |  |  |  |  |  |  |  |  |  |  |  |  |  |  |
| 3-[3-(4- | 2.0 | 9 | 9 | 9 | 9 | 7 | 9 | 9 | 8 | 9 | 9 | 9 | 9 |  | 9 | 4 | 9 | 1 | 2 | 8 |
| Fluoro- | 1.0 | 8 | 8 | 9 | 2 | 3 | 9 | 9 | 1 | 9 | 9 | 9 | 3 |  | 3 | 1 | 7 | 0 | 1 | 2 |
| phenyl- | 0.5 | 3 | 5 | 9 | 1 | 1 | 3 | 9 | 0 | 9 | 9 | 9 | 1 |  | 0 | 0 | 3 | 0 | 0 | 1 |
| ethyl- | 0.25 | 1 | 2 | 2 | 0 | 0 | 2 | 9 | 0 | 8 | 9 | 2 | 0 |  | 0 | 0 | 1 | 0 | 0 | 0 |
| oxy)- | 0.0125 | 0 | 0 | 1 | 0 | 0 | 1 | 9 | 0 | 4 | 9 | 0 | 0 |  | 0 | 0 | 0 | 0 | 0 | 0 |
| phenyl]- | 0.063 | 0 | 0 | 0 | 0 | 0 | 1 | 2 | 0 | 2 | 2 | 0 | 0 |  | 0 | 0 | 0 | 0 | 0 | 0 |
| 1,1-di- |  |  |  |  |  |  |  |  |  |  |  |  |  |  |  |  |  |  |  |  |
| methyl- |  |  |  |  |  |  |  |  |  |  |  |  |  |  |  |  |  |  |  |  |
| urea |  |  |  |  |  |  |  |  |  |  |  |  |  |  |  |  |  |  |  |  |

EXAMPLE 4
Postemergence Herbicidal Activity

By the method of Example 2, the postemergence herbicidal activity of phenylalkoxyphenylurea compounds is evaluated. The data obtained are reported in Table III below, wherein it can be clearly seen that the urea compounds selectively control broadleaf weeds in the presence of graminaceous crops, such as barley, wheat, rice, corn, soybeans, and especially sorghum.

pounds is evaluated, the data obtained are reported in Table IV below, wherein it can be seen that the urea compounds selectively control broadleaf weeds, at the higher rates applied, in the presence of crops, such as barley, wheat, corn, rice, soybeans and sorghum.

TABLE III

Evaluation of the Postemergence Herbicidal Activity of the Compounds of the Invention

| Compound | Rate kg/ha | CB | JW | LA | MG | MU | PI | RW | VL | BY | CN | RI | SO | SY | WH |
|---|---|---|---|---|---|---|---|---|---|---|---|---|---|---|---|
| 1,1-Dimethyl-3-[3-(4-methylphenethyloxy)-phenyl]urea | 2.0 | 3 | 1 | 9 | 9 | 9 | 9 | 4 | 8 | 0 | 0 | 0 | 0 | 7 | 0 |
|  | 1.0 | 9 | X | 9 | 9 | 9 | 9 | 0 | 0 | 0 | 0 | 0 | 0 | 1 | 0 |
|  | 0.5 | X | 0 | 9 | 9 | 9 | 9 | X | 0 | 0 | 0 | 0 | 0 | 0 | 0 |
|  | 0.25 | 7 | X | 3 | 9 | 9 | 6 | 0 | 0 | 0 | 0 | 0 | 0 | 0 | 0 |
|  | 0.125 | X | X | 0 | 2 | X | 3 | X | 0 | 0 | 0 | 0 | 0 | 0 | 0 |
|  | 0.063 | X | 0 | 0 | X | 9 | 0 | 0 | 0 | 0 | 0 | 0 | 0 | 0 | 0 |
| 3-[3-4-Methoxyphenyl-ethyloxy)phenyl]-1,1-dimethylurea | 2.0 | 9 | X | 8 | 9 | 9 | 9 | 9 | 9 | 0 | 1 | 2 | 9 | 0 |  |
|  | 1.0 | 9 | X | X | 9 | 9 | 9 | 9 | 9 | 0 | 0 | 0 | 0 | 0 | 0 |
|  | 0.5 | 9 | X | 9 | 9 | 9 | 6 | 9 | 2 | 0 | 0 | 0 | 0 | 0 | 0 |
|  | 0.25 | X | X | 7 | 4 | 9 | 3 | 9 | 1 | 0 | 0 | 0 | 0 | 0 | 0 |
|  | 0.125 | 3 | X | 4 | X | 9 | 0 | 9 | 0 | 0 | 0 | 0 | 0 | 0 | 0 |
|  | 0.063 | 2 | X | 0 | 0 | 0 | 0 | 3 | 0 | 0 | 0 | 0 | 0 | 0 | 0 |
| 1,1-Dimethyl-3-[3-(β-methylphenylethoxy)-phenyl]urea | 2.0 | 9 | 9 | 9 | 9 | 9 | 9 | 9 | 9 | 0 | 3 | 9 |  | 9 | 0 |
|  | 1.0 | X | X | 9 | X | 9 | 9 | 9 | 9 | 0 | 9 | 6 |  | 9 | 0 |
|  | 0.5 | X | X | 9 | X | 9 | 9 | 9 | 7 | 0 | 9 | 3 |  | 0 | 0 |
|  | 0.25 | X | X | 9 | 9 | 9 | 6 | 9 | 0 | 0 | 2 | 2 |  | 0 | 0 |
|  | 0.125 | X | X | 6 | 2 | 9 | 0 | 3 | 0 | 0 | 0 | 0 |  | 0 | 0 |
|  | 0.063 | X | X | X | X | 0 | 0 | 3 | 0 | 0 | 0 | 0 |  | 0 | 0 |
| 1,1-Dimethyl-3-[3-(α-methylphenyloxy)-phenyl]urea | 2.0 | 9 | 9 | 9 | 9 | 9 | 9 | 9 | 9 | 0 | 0 | 2 | 1 | 1 | 0 |
|  | 1.0 | 9 | 9 | 9 | 6 | 9 | 9 | 9 | 9 | 0 | 0 | 0 | 0 | 1 | 0 |
|  | 0.5 | 9 | 9 | 9 | 9 | 9 | 9 | 7 | 9 | 0 | 0 | 1 | 0 | 0 | 0 |
|  | 0.25 | 8 | 9 | 9 | 9 | 9 | 9 | 7 | 6 | 0 | 1 | 1 |  | 0 | 0 |
|  | 0.125 | 8 | 9 | 9 | 9 | 0 | 4 | 2 | 2 | 0 | 0 | 0 | 0 | 0 | 0 |
|  | 0.063 | 0 | 9 | 9 | 3 | 0 | 0 | 0 | 0 | 0 | 0 | 0 | 0 | 0 | 0 |
| 3-[3-(α-Ethylphenyl-ethyloxy)phenyl]-1,1-dimethylurea | 2.0 | 4 | 9 | 9 | 8 | 9 | 8 | 9 | 9 | 0 | 9 | 1 | 0 | 2 | 0 |
|  | 1.0 | 3 | 9 | 9 | 8 | 9 | 9 | 2 | 9 | 0 | 9 | 0 | 0 | 1 | 0 |
|  | 0.5 | 3 | 3 | 7 | 7 | 9 | 3 | 1 | 7 | 0 | 1 | 0 | 0 | 0 | 0 |
|  | 0.25 | 0 | 2 | 6 | 6 | 2 | 0 | 0 | 2 | 0 | X | 0 | 0 | 0 | 0 |
|  | 0.125 | 0 | 2 | 0 | 0 | 0 | 0 | 0 | 0 | 0 | 0 | 0 | 0 | 0 | 0 |
|  | 0.063 | 0 | 2 | 0 | 0 | 0 | 0 | 0 | 0 | 0 | 0 | 0 | 0 | 0 | 0 |
| 3-{3-[3-(4-Methoxy-phenyl)propoxyl]phenyl}-1,1-dimethylurea | 2.0 | 9 | 9 | 9 | 9 | 9 | 9 | 9 | 9 | 0 | 0 | 0 | 0 | 3 | 0 |
|  | 1.0 | 2 | 9 | 9 | 9 | 9 | 9 | 9 | 8 | 0 | 0 | 0 | 0 | 8 | 0 |
|  | 0.5 | 2 | 9 | 9 | 6 | 9 | 9 | 7 | 8 | 0 | 0 | 0 | 0 | 3 | 0 |
|  | 0.25 | 9 | 9 | 9 | 9 | 9 | 9 | 3 | 7 | 0 | 0 | 0 | 0 | 3 | 0 |
|  | 0.125 | 0 | 9 | 9 | X | 9 | 9 | 4 | 7 | 0 | 0 | 0 | 0 | 2 | 0 |
|  | 0.063 | 9 | 9 | 7 | X | 9 | 7 | 4 | 3 | 0 | 0 | 0 | 0 | 0 | 0 |
| 3-[3-(4-Chlorophenyl-ethyloxy)phenyl]-1,1-dimethylurea | 2.0 | 9 | 9 | 9 | 9 | 9 | 9 | 9 | 9 | 0 | 0 | 3 | 6 | 9 | 0 |
|  | 1.0 | 9 | 9 | 9 | 9 | 9 | 9 | 9 | 3 | 0 | 0 | 3 | 0 | 1 | 0 |
|  | 0.5 | 6 | 9 | 9 | 3 | 9 | 9 | 9 | 7 | 0 | 0 | 3 | 0 | 9 | 0 |
|  | 0.25 | 3 | 9 | 9 | X | 9 | 9 | 9 | 7 | 0 | 0 | 2 | 0 | 2 | 0 |
|  | 0.125 | X | 9 | 9 | 3 | 9 | 9 | 9 | 9 | 0 | 0 | 2 | 0 | 1 | 0 |
|  | 0.063 | 3 | 9 | 9 | 3 | 9 | 9 | 8 | 8 | 0 | 0 | 2 | 0 | 2 | 0 |
| 3-[3-(3-Methoxyphenyl-ethyloxy)phenyl]-1,1-dimethylurea | 2.0 | 9 | 9 | 9 | 9 | 9 | 9 | 9 | 8 | 2 | 1 | 4 | 0 | 8 | 0 |
|  | 1.0 | 8 | 9 | 9 | 8 | 9 | 9 | 9 | 8 | 1 | 0 | 0 | 0 | 8 | 0 |
|  | 0.5 | 0 | 9 | 9 | 8 | 9 | 9 | 9 | 8 | 0 | 0 | 0 | 0 | 0 | 0 |
|  | 0.25 | 0 | 9 | 9 | 4 | 9 | 9 | 0 | 8 | 0 | 0 | 0 | 0 | 0 | 0 |
|  | 0.125 | 0 | 9 | X | 4 | 9 | 9 | X | 0 | 0 | 0 | 0 | 0 | 0 | 0 |
|  | 0.063 | 0 | X | 0 | 2 | 0 | 0 | 0 | 0 | 0 | 0 | 0 | 0 | 0 | 0 |

EXAMPLE 5

Preemergence Herbicidal Activity

By the method of Example 3, the preemergence herbicidal activity of m-phenylalkoxyphenylurea com-

TABLE IV

Evaluation of the Preemergence Herbicidal Activity of the Compounds of the Invention

| Compound | Rate kg/ha | CB | JW | LA | MG | MU | PI | RW | VL | BY | CN | RI | SO | SY | WH |
|---|---|---|---|---|---|---|---|---|---|---|---|---|---|---|---|
| 1,1-Dimethyl-3-[3-(4-methylphenylethyloxy)-phenyl]urea | 2.0 | 0 | 9 | 9 | 9 | 9 | 9 | 9 | 9 | 0 | 0 | 1 | 0 | 1 | 0 |
|  | 1.0 | 0 | 9 | 9 | 2 | 9 | 9 | 2 | 0 | 0 | 0 | 0 | 0 | 0 | 0 |
|  | 0.5 | 0 | 9 | 9 | 1 | 9 | 9 | 0 | 0 | 0 | 0 | 0 | 0 | 0 | 0 |
|  | 0.25 | 0 | 0 | 8 | 0 | 9 | 9 | 0 | 0 | 0 | 0 | 0 | 0 | 0 | 0 |
|  | 0.125 | 0 | 0 | 8 | 0 | 9 | 3 | 0 | 0 | 0 | 0 | 0 | 0 | 0 | 0 |
|  | 0.063 | 0 | 0 | 4 | 0 | 0 | 0 | 0 | 0 | 0 | 0 | 0 | 0 | 0 | 0 |
| 3-[3-(4-Methoxyphenyl-ethyloxy)phenyl]-1,1-dimethylurea | 2.0 | 4 | 9 | 9 | 9 | 9 | 9 | 9 | 9 | 1 | 0 | 2 | 0 | 0 | 2 |
|  | 1.0 | 0 | 3 | 9 | 9 | 9 | 9 | 0 | 8 | 0 | 0 | 0 | 0 | 0 | 1 |
|  | 0.5 | 0 | 0 | 9 | 3 | X | 9 | 0 | 3 | 0 | 0 | 0 | 0 | 0 | 0 |
|  | 0.25 | 0 | 0 | 9 | 0 | 8 | 9 | 0 | 0 | 0 | 0 | 0 | 0 | 0 | 0 |

TABLE IV-continued
Evaluation of the Preemergence Herbicidal Activity of the Compounds of the Invention

| Compound | Rate kg/ha | CB | JW | LA | MG | MU | PI | RW | VL | BY | CN | RI | SO | SY | WH |
|---|---|---|---|---|---|---|---|---|---|---|---|---|---|---|---|
| | 0.125 | 0 | 0 | 8 | 0 | 6 | 0 | 0 | 0 | 0 | 0 | 0 | 0 | 0 | 0 |
| | 0.063 | 0 | 0 | 7 | 0 | 0 | 0 | 0 | 0 | 0 | 0 | 0 | 0 | 0 | 0 |
| 1,1-Dimethyl-3-[3-(β-methylphenylethyloxy)-phenyl]urea | 2.0 | 1 | 9 | 9 | 3 | 9 | 9 | 9 | 9 | 1 | 0 | 0 | 0 | 3 | 2 |
| | 1.0 | 1 | 9 | 9 | 3 | 9 | 9 | 4 | 8 | 0 | 0 | 0 | 0 | 0 | 0 |
| | 0.5 | 0 | 9 | 9 | 0 | 9 | 9 | 4 | 7 | 0 | 0 | 0 | 0 | 0 | 0 |
| | 0.25 | 0 | 9 | 9 | 0 | 9 | 9 | 0 | 0 | 0 | 0 | 0 | 0 | 0 | 0 |
| | 0.125 | 0 | 9 | 9 | 0 | 1 | 7 | 0 | 0 | 0 | 0 | 0 | 0 | 0 | 0 |
| | 0.063 | 0 | 9 | 9 | 0 | 0 | 0 | 0 | 0 | 0 | 0 | 0 | 0 | 0 | 0 |
| 1,1-Dimethyl-3-[3-(α-methylphenylethyloxy)-phenyl]urea | 2.0 | 0 | 8 | 9 | 9 | 9 | 9 | 0 | 9 | 0 | 0 | 1 | 0 | 0 | 0 |
| | 1.0 | 0 | 8 | 9 | 0 | 9 | 9 | 0 | 9 | 0 | 0 | 0 | 0 | 0 | 0 |
| | 0.5 | 0 | 9 | 9 | 0 | 9 | 9 | 0 | 0 | 0 | 0 | 0 | 0 | 0 | 0 |
| | 0.25 | 0 | 9 | 9 | 0 | 4 | 9 | 0 | 0 | 0 | 0 | 0 | 0 | 0 | 0 |
| | 0.125 | 0 | 0 | 9 | 0 | 0 | 9 | 0 | 0 | 0 | 0 | 0 | 0 | 0 | 0 |
| | 0.063 | 0 | 0 | 2 | 0 | 0 | 2 | 0 | 0 | 0 | 0 | 0 | 0 | 0 | 0 |
| 3-[3-(α-Ethylphenyl-ethyloxy)phenyl]-1,1-dimethylurea | 2.0 | 0 | 9 | 9 | 9 | 9 | 3 | 0 | 9 | 0 | 0 | 0 | 0 | 0 | 0 |
| | 1.0 | 0 | 6 | 9 | 0 | 3 | 2 | 0 | 0 | 0 | 0 | 0 | 0 | 0 | 0 |
| | 0.5 | 0 | 0 | 9 | 0 | 2 | 0 | 0 | 0 | 0. | 0 | 0 | 0 | 0 | 0 |
| | 0.25 | 0 | 0 | 9 | 0 | 1 | 0 | 0 | 0 | 0 | 0 | 0 | 0 | 0 | 0 |
| | 0.125 | 0 | 0 | 9 | 0 | 0 | 0 | 0 | 0 | 0 | 0 | 0 | 0 | 0 | 0 |
| | 0.063 | 0 | 0 | 3 | 0 | 0 | 0 | 0 | 0 | 0 | 0 | 0 | 0 | 0 | 0 |
| 3-{3-[3-(4-Methoxy-phenyl)propoxy]phenyl}-1,1-dimethylurea | 2.0 | 0 | 9 | 9 | 9 | 9 | 9 | 2 | 7 | 0 | 0 | 0 | 0 | 0 | 0 |
| | 1.0 | 0 | 9 | 9 | 2 | 9 | 9 | 0 | 0 | 0 | 0 | 0 | 0 | 0 | 0 |
| | 0.5 | 0 | 9 | 9 | 0 | 9 | 9 | 0 | 0 | 0 | 0 | 0 | 0 | 0 | 0 |
| | 0.25 | 0 | 0 | 9 | 0 | 0 | 9 | 0 | 0 | 0 | 0 | 0 | 0 | 0 | 0 |
| | 0.125 | 0 | 0 | 9 | 0 | 0 | 0 | 0 | 0 | 0 | 0 | 0 | 0 | 0 | 0 |
| | 0.063 | 0 | 0 | 6 | 0 | 0 | 0 | 0 | 0 | 0 | 0 | 0 | 0 | 0 | 0 |
| 3-[3-(4-Chlorophenyl-ethoxy)phenyl]-1,1-dimethylurea | 2.0 | 0 | 9 | 9 | 9 | 9 | 9 | 2 | 8 | 0 | 0 | 0 | 0 | 0 | 0 |
| | 1.0 | 9 | 9 | 9 | 3 | 9 | 9 | 9 | 6 | 0 | 0 | 0 | 0 | 0 | 0 |
| | 0.5 | 0 | 9 | 9 | 0 | 9 | 9 | 2 | 0 | 0 | 0 | 0 | 0 | 0 | 0 |
| | 0.25 | 0 | 9 | 9 | 0 | 9 | 9 | 9 | 0 | 0 | 0 | 0 | 0 | 0 | 0 |
| | 0.125 | 0 | 0 | 9 | 0 | 0 | 4 | 0 | 0 | 0 | 0 | 0 | 0 | 0 | 0 |
| | 0.063 | 0 | 9 | 9 | 0 | 0 | 0 | 0 | 0 | 0. | 0 | 0 | 0 | 0 | 0 |
| 3-[3-(3-Methoxyphenyl-ethyloxy)phenyl]-1,1-dimethylurea | 2.0 | 2 | 9 | 9 | 9 | 9 | 9 | 9 | 9 | 7 | 1 | 2 | 0 | 0 | 3 |
| | 1.0 | 0 | 9 | 9 | 0 | 9 | 9 | 7 | 0 | 4 | 0 | 1 | 0 | 0 | 2 |
| | 0.5 | 0 | 9 | 9 | 0 | 9 | 9 | 0 | 0 | 0 | 0 | 0 | 0 | 0 | 0 |
| | 0.25 | 0 | 9 | 9 | 0 | 3 | 9 | 0 | 0 | 0 | 0 | 0 | 0 | 0 | 0 |
| | 0.125 | 0 | 0 | 9 | 0 | 0 | 8 | 0 | 0 | 0 | 0 | 0 | 0 | 0 | 0 |
| | 0.063 | 0 | 0 | 2 | 0 | 0 | 0 | 0 | 0 | 0 | 0 | 0 | 0 | 0 | 0 |

We claim:

1. A method for the preparation of compounds of formula:

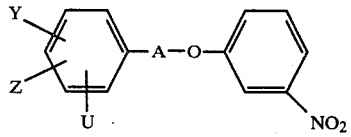

wherein Y is hydrogen, halogen, $C_1$–$C_4$ alkyl, $C_3$–$C_5$ alkenyl, $C_3$–$C_5$ alkynyl, $C_1$–$C_4$ alkoxy, $CH_3S$, $CF_3$, CN, $NH_2$, $OCF_2H$, $OCF_3$ or $OCF_2Cl$; Z is hyrogen, $C_1$–$C_4$ alkyl, $C_1$–$C_4$ alkoxy, halogen, or $CF_3$; U is hydrogen, $C_1$–$C_4$ alkyl, $C_1$–$C_4$ alkoxy or halogen; A is $C_2$–$C_4$ alkylene, straight chain or branched; comprising reacting a compound of formula:

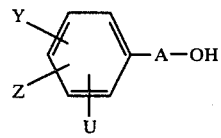

wherein Y, Z, U and A are as defined above with an equimolar amount of m-dinitrobenzene in the presence of an equimolar amount of an alkali metal hydroxide or an alkali metal alkoxide and in the presence of a polar solvent of hexamethylphosphoramide, dimethylformamide, dimethyl sulfoxide, acetonitrile or mixtures thereof in the temperature range of from 20° C. to 80° C.

2. A method according to claim 1, wherein Y is hydrogen, Cl, F, $CH_3$ or $CH_3O$; Z and U are both hydrogen; the alkali metal alkoxide is potassium t-butoxide; the solvent is hexamethylphosphoramide, and the temperature range is 20° C. to 30° C.

3. The method according to claim 1, wherein the compound is 3-(phenylethloxy)nitrobenzene.

4. A method according to claim 1, wherein the compound is 3-(4-methylphenylethyloxy)nitrobenzene.

5. A method according to claim 1, wherein the compound is 3-(4-methoxyphenylethyloxy)nitrobenzene.

6. A method according to claim 1, wherein the compound is 3-(4,α-dimethylphenylethyloxy)nitrobenzene.

7. A method according to claim 1, wherein the compound is 3-(4,β-dimethylphenylethyloxy)nitrobenzene.

8. A method according to claim 1, wherein the compound is 3-(4-methoxy-α-methylphenylethyloxy)nitrobenzene.

9. A method according to claim 1, wherein the compound is 3-(4-methoxy-p-methylphenylethyloxy)nitrobenzene.

* * * * *